(12) United States Patent
Miyatani et al.

(10) Patent No.: US 8,087,334 B2
(45) Date of Patent: Jan. 3, 2012

(54) SECTIONING INSTRUMENT

(75) Inventors: Tatsuya Miyatani, Chiba (JP);
Tetsumasa Ito, Chiba (JP); Hirohito Fujiwara, Chiba (JP); Koji Fujimoto, Chiba (JP)

(73) Assignee: Seiko Instruments Inc., Chiba (JP)

( * ) Notice: Subject to any disclaimer, the term of this patent is extended or adjusted under 35 U.S.C. 154(b) by 272 days.

(21) Appl. No.: 11/643,922

(22) Filed: Dec. 20, 2006

(65) Prior Publication Data

US 2007/0157786 A1    Jul. 12, 2007

(30) Foreign Application Priority Data

Dec. 28, 2005    (JP) .................................. 2005-377722

(51) Int. Cl.
*G01N 1/06* (2006.01)
(52) U.S. Cl. ..................... 83/915.5; 83/112; 83/155.1
(58) Field of Classification Search ............ 83/109–113, 83/155, 155.1, 915, 932
See application file for complete search history.

(56) References Cited

U.S. PATENT DOCUMENTS

| | | | | |
|---|---|---|---|---|
| 2,318,003 A | * | 5/1943 | Mahler | 83/92 |
| 3,667,330 A | * | 6/1972 | Kobernick | 83/98 |
| 5,156,019 A | * | 10/1992 | McCormick | 62/320 |
| 5,461,953 A | * | 10/1995 | McCormick | 83/36 |
| 5,713,255 A | * | 2/1998 | Izvozichikov et al. | 83/24 |
| 5,740,708 A | * | 4/1998 | Tabone | 83/100 |
| 6,413,566 B2 | * | 7/2002 | Caridis et al. | 426/518 |
| 2006/0086221 A1 | * | 4/2006 | Kong et al. | 83/401 |

FOREIGN PATENT DOCUMENTS

| | | |
|---|---|---|
| DE | 8217320 U1 | 12/1982 |
| DE | 4307738 * | 9/1993 |
| DE | 4307738 A1 | 9/1993 |
| DE | 19630382 A1 | 2/1998 |
| GB | 1293570 | 10/1972 |
| JP | S49-28711 | 7/1974 |
| JP | H09-304246 | 11/1997 |
| JP | 2000-346764 A | 12/2000 |

OTHER PUBLICATIONS

European Search Report issued Feb. 27, 2008 in European application No. 06256604.7.

* cited by examiner

*Primary Examiner* — Edward Landrum
(74) *Attorney, Agent, or Firm* — Brinks Hofer Gilson & Lione

(57) ABSTRACT

A sectioning instrument fabricates a section having an accurate and uniform thickness to be carried to a next step automatically without deforming a surface of an embedded block and while observing the surface of the embedded block. The sectioning instrument includes a sample base for fixing an embedded block, a cutter for fabricating a section by sectioning the embedded block, a carrier for carrying the section, and a feed mechanism for moving the sample base in a predetermined feed direction. The carrier includes a belt, a direction switching portion provided on an upper side of the cutter, and a rear roller. The belt is inserted to between the cutter and the direction switching portion from a rear side of the cutter, folded back to an upper side by the direction switching portion and is reeled back to the rear side of the cutter by the rear roller substantially in parallel with the feed direction of the feed mechanism in a plane view.

12 Claims, 8 Drawing Sheets

SECTIONING INSTRUMENT

This application claims priority under 35 U.S.C. §119 to Japanese Patent Application No. JP2005-377722 filed Dec. 28, 2005, the entire content of which is hereby incorporated by reference.

BACKGROUND OF THE INVENTION

1. Field of the Invention

The present invention relates to a sectioning instrument for fabricating a section by sectioning an embedded block embedded with a living body sample sampled from the human body, an experimental animal or the like and carrying the fabricated section to a next step.

2. Description of the Related Arts

In a related art, there is known a method of sectioning an embedded block embedded with a living body sample by an embedding medium to a section having a thickness as extremely thin as several μm, thereafter, observing a sample constituted by dissolving the embedding medium as one of methods of inspecting and observing the living body sample sampled from the human body, an experimental animal or the like. As details of a step of fabricating the section, a section having a thickness of about 3 through 5 μm is fabricated by fixing the embedded block to a sample base and moving a cutter by a predetermined moving speed. Further, the section fabricated in this way is caught by a slender string or the like to be taken out and is carried to successive steps of an elongating step, a drying step and the like. Therefore, in the related art, the step of taking out and carrying the fabricated section is carried out by manual operation since the section is extremely thin, and damage of curl, wrinkle, break or the like is liable to be brought about. On the other hand, for example, in a preclinical test, several hundreds pieces of the embedded blocks are fabricated per test, and several sheets of the sections are fabricated per the embedded block. Therefore, an operator needs to fabricate an enormous number of sheets of the sections to be carried to successive steps and the steps have been tried to be automated.

For example, there is proposed an apparatus including a cutter for sectioning an embedded block, a sample base fixed with the embedded block and moved reciprocally relative to the cutter, a tape having an adhering layer and extended between a supply roll and a collect roll above the sample base, and a press apparatus for pressing the tape to a surface of the embedded block above the embedded block (see, for example, JP-B-49-28711). According to the apparatus, the fabricated section is adhered to the tape to be able to be carried by pressing the tape to the surface of the embedded block by the press apparatus frontward from a cut blade of the cutter in sectioning the embedded block by the cutter.

Further, there is proposed a method of fabricating a section of charging an embedded block and a tape by charges having different polarities, bringing the tape into contact to be adhered to a sectioning start portion by reducing a tension exerted to the tape at an initial stage of sectioning, increasing the tension in the midst of sectioning, and separating the section adhered to the tape from a scoop face of a cutter (see, for example, Japanese Patent Publication No. 3560728).

However, according to both of the apparatus and the method according to Patent Reference 1 and Patent Reference 2, it is necessary to adhere the tape or adhere the tape by an electrostatic force by pressing the tape to the surface of the embedded block before being sliced by the cutter, there is a concern of deforming the surface of the embedded block by pressing the tape to the embedded block. That is, there poses a problem that the section cannot be fabricated accurately and by a uniform thickness by deforming the surface of the embedded block. Further, there poses a problem that the surface of the embedded block cannot be observed in fabricating the section since the sample embedded in the embedded block is brought into a state of being covered always by the tape or the cutter by disposing the tape upward from the embedded block.

SUMMARY OF THE INVENTION

The invention has been carried out in view of the above-described situation and it is an object thereof to provide a sectioning instrument capable of fabricating a section having an accurate and uniform thickness without deforming a surface of an embedded block and while observing the surface of the embedded block and carrying the section automatically to a next step.

In order to resolve the above-described problem, the invention proposes the following means.

According to the invention, there is provided a sectioning instrument comprising a sample base for fixing an embedded block embedded with a living body sample, a cutter for fabricating a section by sectioning the embedded block fixed to the sample base, carrying means for carrying the section fabricated by the cutter to a rear side of the cutter to deliver to a next step, and a feed mechanism for moving either one of the sample base or the cutter and the carrying means in a predetermined feed direction and sectioning the embedded block by the cutter, wherein the carrying means comprises a belt mounted with the section for carrying the section, a direction switching portion provided on an upper side of the cutter substantially in parallel with a direction of a cut blade of the cutter, proximate to the cut blade and having a gap capable of inserting the belt between the cutter and the direction switching portion, and a rear roller provided in the rear side of the cutter, wherein the belt is made to travel from the rear side of the cutter to the cutter, inserted between the cutter and the direction switching portion, folded back to an upper side by the direction switching portion, and reeled back to the rear side of the cutter by the rear roller.

According to the sectioning instrument according to the invention, the embedded block fixed to the sample base is sliced by the cutter to form the section by moving either one of the sample base or the cutter in the feed direction by the feed mechanism. At this occasion, a sliced surface of the embedded block is brought to an exposed state, there is not constructed a constitution of sectioning the embedded block in a state of pressing the surface of the sliced block and therefore, the embedded block can be sliced by an accurate and uniform thickness while observing the surface of the embedded block. Further, in accordance of movement of the fabricated section to a rear side in the feed direction of the cutter relatively, the section can be brought into contact with the belt folded back by the direction switching portion and reeled back in the feed direction on the upper side of the cutter, mounted thereon and carried to the rear side of the cutter along with the belt.

Further, according to the slice piece fabricating apparatus, it is preferable that a traveling speed of the belt of the carrying means is set to a speed substantially equal to a moving speed by the feed mechanism.

According to the sectioning instrument according to the invention, the traveling speed of the belt is a speed substantially equal to the moving speed by the feed mechanism, that is, a speed of fabricating the section fabricated by the cutter. Therefore, the fabricated section is not cut by being pulled by the belt because the traveling speed of the belt is faster, or the fabricated section is not wrinkled between the belt and the cut blade of the cutter because the traveling speed of the belt is slower.

Further, according to the sectioning instrument, it is preferable that a position on a front side of the cutter opposed to the direction switching portion is provided with blowing means for blowing wind to the section sliced by the cutter to press the section to the belt folded back by the direction switching portion of the carrying means.

According to the sectioning instrument according to the invention, the fabricated section is pressed to the belt disposed on the rear side of the section by blowing wind by the blowing means. Therefore, the fabricated section is further firmly mounted on the belt and is carried to the rear side of the cutter by the belt. Particularly, although there is a case in which the fabricated section is curled to the front side of the cutter in sectioning by the cutter, the section can be prevented from being curled by blowing wind by the blowing means.

Further, according to the sectioning instrument, it is preferable to further comprise a fixed base for supporting the cutter, and a holder a section of which is substantially in a channel-like shape projecting both end portions to a lower side and formed with a recess portion at a center thereof, in which the both end portions are brought into contact with an upper face of the cutter, the cutter is squeezed between the holder and the fixed base, and which is formed with a through hole penetrated from a rear side to a front side of the cutter between the holder and the cutter by the recess portion, and a front end of the holder is formed with the direction switching portion, the belt is inserted through the through hole from the rear side of the cutter and is folded back by the direction switching portion.

According to the sectioning instrument according to the invention, the belt passes through the through hole formed between the holder and the cutter from the rear side of the cutter and is folded back by the direction switching portion formed at the front end of the holder. Therefore, the belt and the cutter can be arranged to be further proximate to each other at a vicinity of the cut blade of the cutter and therefore, the section fabricated by the cutter and moved to the rear side can further firmly be mounted on the belt.

Further, according to the sectioning instrument, it is preferable that the carrying means comprises a supply roller wound with the belt for supplying the belt, and the belt is made to travel from the supply roller to the direction switching portion, folded back by the direction switching portion and is wound by the rear roller.

According to the sectioning instrument according to the invention, the belt is supplied from the supply roller by winding the belt by rotating the rear roller and is folded back at the direction switching portion. Further, the mounted fabricated piece can be carried to a position of being wound by the rear roller by mounting the fabricated section thereon.

Further, according to the sectioning instrument, it is preferable that a direction of the cut blade of the cutter is provided to include a predetermined draw angle relative to an axis line orthogonal to the feed direction of the feed mechanism on a cut face formed by the cutter, a direction of supplying the belt traveling from the supply roller to the direction switching portion is set to be inclined to an axis line orthogonal to the direction of the cut blade by an angle substantially equal to the draw angle, and the belt folded back by the direction switching portion is reeled back in parallel with the feed direction of the feed mechanism by the rear roller in a plane view thereof.

According to the sectioning instrument according to the invention, since the cutter is provided to include the draw angle, a resistance in sectioning the embedded block can be restrained and the embedded block can be sliced by an accurate and uniform thickness and by an excellent cut face. At this occasion, the direction switching portion is provided to be proximate to the cut blade substantially in parallel with the direction of the cut blade of the cutter and therefore, the section fabricated by the cutter can firmly be mounted on the belt. On the other hand, the belt is reeled back in the direction of fabricating the section by the rear roller, that is, the feed direction of the feed mechanism. Therefore, the section fabricated by the cutter and carried by being brought into contact with the belt is carried in a state of being mounted on the belt without being cut by operating twist or the like by traveling of the belt. Further, the belt is not twisted even when the direction switching portion is provided to include the draw angle along with the cut blade by inclining the supply direction in which the belt travels from the supply roller to the direction switching portion by the angle substantially equal to the draw angle relative to the axis line orthogonal to the direction of the cut blade. Therefore, the belt can smoothly be made to travel from the supply roller to the direction switching portion, further, the direction switching portion to the rear roller.

Further, according to the sectioning instrument, it is preferable that the belt of the carrying means is an endless belt wound between the rear roller and the direction switching portion.

According to the sectioning instrument according to the invention, by constituting the belt by the endless belt wound from the rear roller to the direction switching portion, the belt can endlessly made to travel and the fabricated section can continuously be carried.

Further, according to the sectioning instrument, it is preferable that a direction of the cut blade of the cutter is provided to include a predetermined draw angle relative to an axis line orthogonal to the feed direction of the feed mechanism on a cut face formed by the cutter, and the belt of the carrying means is formed by a plurality of ring-like members substantially in a string-like shape arranged at predetermined intervals thereamong, respective of the ring-like members are provided with different peripheral lengths in correspondence with a distance between the rear roller and the direction switching portion, and reeled back substantially in parallel with the feed direction of the feed mechanism by the rear roller in a plane view thereof.

According to the sectioning instrument according to the invention, since the cutter is provided to include the draw angle, the resistance in sectioning the embedded block can be restrained and the embedded block can be sliced by further accurate and uniform thickness and by an excellent cut face. On the other hand, the belt is reeled back in the direction of fabricating the section, that is, in the feed direction of the feed mechanism by the rear roller. Therefore, the section fabricated by the cutter and carried by being brought into contact with the belt is carried in a state of being mounted on the belt without being cut by operating twist or the like by traveling of the belt. At this occasion, since the direction switching portion is substantially in parallel with the cut blade of the cutter, the rear roller and the direction switching portion wound with the belt are not brought into a parallel positional relationship. However, since respective of the plurality of ring-like members forming the belt are provided with the different peripheral lengths in correspondence with the distance between the rear roller and the direction switching portion, the belt can be made to travel endlessly between the rear roller and the direction switching portion smoothly without being twisted.

Further, according to the sectioning instrument, it is preferable that the rear side of the cutter is provided with a liquid tank filled with a liquid, and the belt of the carrying means is dipped in the liquid of the liquid tank at the rear roller or between the rear roller and the direction switching portion.

According to the sectioning instrument according to the invention, by carrying the section mounted on the belt to the liquid of the liquid tank along with the belt, the section can be detached from the state of being mounted on the belt into the liquid of the liquid tank and can be delivered to a next step.

According to the sectioning instrument of the invention, as the carrying means, the direction switching portion and the rear roller are provided, and by folding back the belt to the upper side of the cutter and reeling back the belt to the rear side of the cutter, while observing the surface of the embedded block, the section can be fabricated by the cutter and carried. Further, the surface of the embedded block is not pressed at all in sectioning the embedded block by the cutter. Therefore, the section can automatically be fabricated by the accurate and uniform thickness and can be carried to a next step.

DESCRIPTION OF THE PREFERRED EMBODIMENTS

First Embodiment

Figure 1:
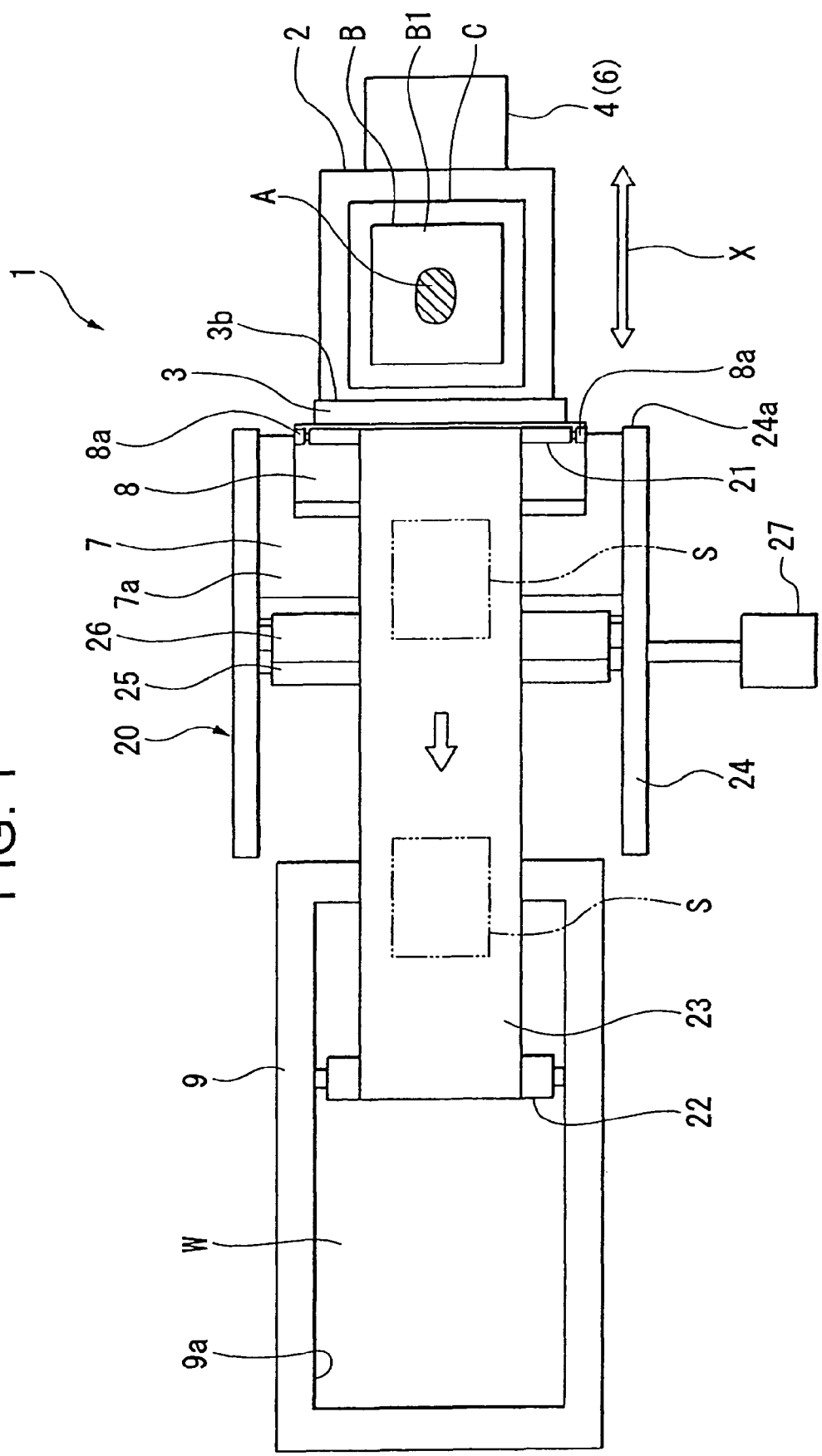
FIG. 1 is a plane view of a sectioning instrument according to a first embodiment of the invention.
Figure 2:
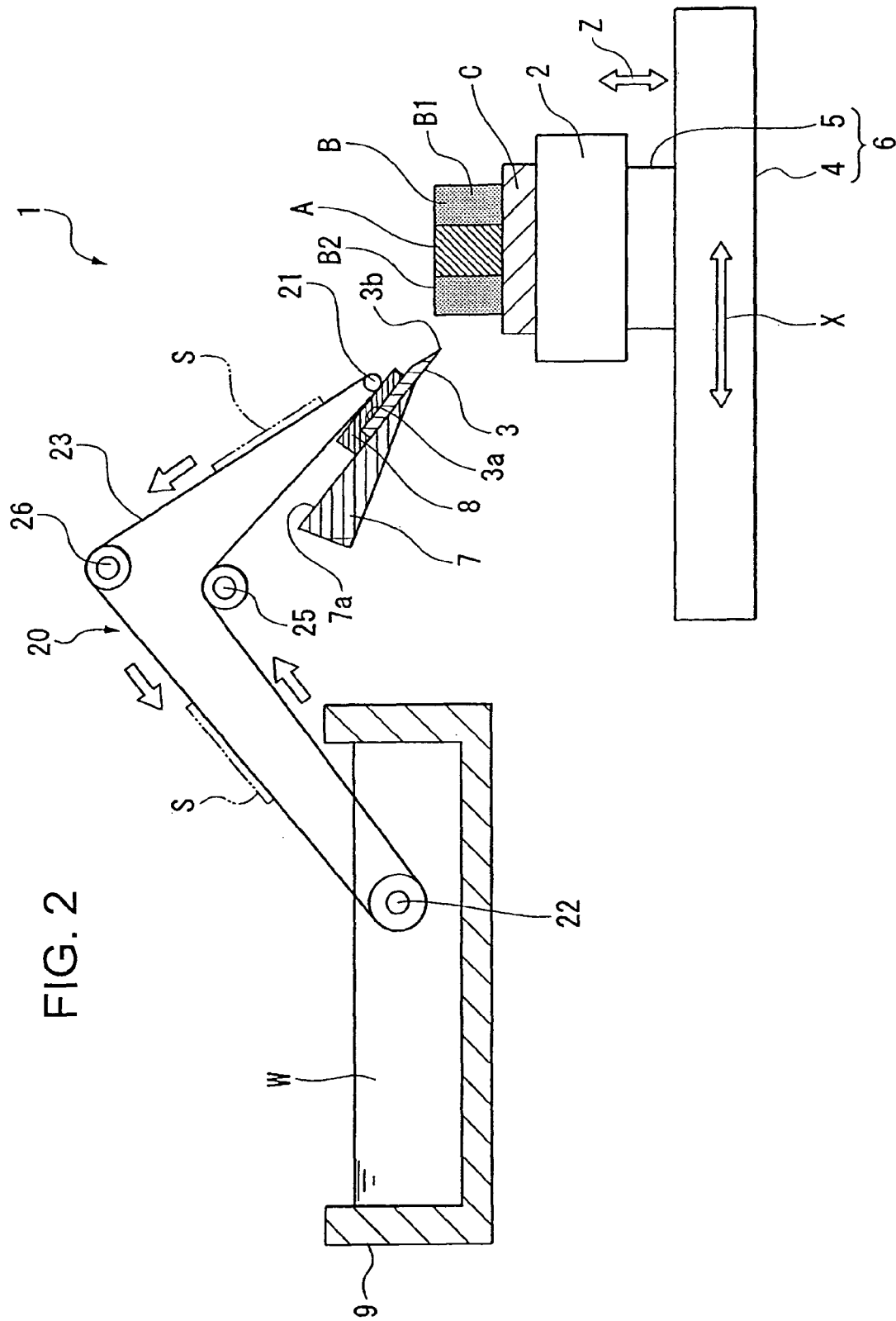
FIG. 2 is a sectional view of the sectioning instrument according to the first embodiment of the invention.

FIG. 1 and FIG. 2 show a first embodiment according to the invention. A sectioning instrument 1 shown in FIG. 1 is an apparatus for fabricating an extremely thin section having a thickness of 3 through 5 µm from an embedded block B embedded with a living body sample A, sectioning a section from the embedded block B and carrying the section to a next step automatically in a procedure of inspecting and observing the living body sample A included in section. The living body sample A is, for example, a tissue of an organ or the like taken out from the human body, an experimental animal or the like and is pertinently selected in a medical field, a drug field, a food field, or a biological field. Further, the embedded block B is constituted by enveloping the living body sample A by an embedding medium B1, that is, covering to harden a surrounding thereof. Further in details, such an embedded block B is fabricated as follows. First, protein constituting the living body sample A is fixed by dipping a block of the living body sample A in formalin. Further, the tissue is cut to a pertinent size after having been brought into a hard state. Finally, the cut living body sample A in which the embedding medium B1 substitutes for moisture at inside thereof is embedded in a dissolved embedding medium B1 to be hardened to thereby fabricate the embedded block B. Here, the embedding medium B1 is constituted by a material which can easily be liquefied and cooled to solidify and is dissolved by being dipped in ethanol as described above, and is a resin, paraffin or the like. A constitution of the sectioning instrument 1 will be explained as follows.

As shown by FIG. 1 and FIG. 2, the sectioning instrument 1 includes a sample base 2 for fixing a cassette C mounted with the embedded block B, a cutter 3 for sectioning the embedded block B, and carrying means 20 for carrying a section S sliced from the embedded block B by the cutter 3. The sample base 2 can position the cassette C mounted with the embedded block B to be fixed. Further, a feed mechanism 6 having X stage 4 and Z stage 5 is provided on a lower side of the sample base 2, and can adjust a position of the embedded block B fixed to the sample base 2 in sectioning feed direction X and height direction Z and feed the embedded block B by a predetermined moving speed in feed direction X. Further, the sectioning instrument 1 includes a fixed base 7 for supporting the cutter 3, a holder 8 is provided at an upper face 7a of the fixed base 7 for squeezing to fix the cutter 3 between the holder 8 and the fixed base 7 by being brought into contact with an upper face 3a of the cutter 3. The cutter 3 is fixed to make a direction of the cut blade 3b at a front end portion thereof orthogonal to feed direction X. Further, a liquid tank 9 filled with water W is provided rearward from the cutter 3.

The carrying means 20 includes a direction switching roller 21 constituting a direction switching portion provided to be proximate to the cut blade 3b substantially in parallel with a direction of the cut blade 3b of the cutter 3, a rear roller 22 provided rearward from the cutter 3, and an endless belt 23 wound between the direction switching roller 21 and the rear roller 22. As shown by FIG. 1, the direction switching roller 21 and the rear roller 22 are arranged with the endless belt 23 to be able to travel substantially in parallel with feed direction X of the feed mechanism 6 in a plane view thereof. Further, as shown by FIG. 1 and FIG. 2, an upper face of the holder 8 is provided with a pair of support members 8a to project upward. Further, the direction switching roller 21 is axially attached rotatably to the support member 8a by providing a gap capable of inserting the endless belt 23 between the direction switching roller 21 and the holder 8 of the cutter 3. Further, the rear roller 22 is axially attached rotatably to an inner wall 9a of the liquid tank 9 and is brought into a state of being dipped to water W of the liquid tank 9. Further, middle rollers 25, 26 disposed upward from the direction switching roller 21 and the rear roller 22 and axially attached rotatably to a frame 24 are provided between the direction switching roller 21 and the rear roller 22. Further, also the fixed base 7 for supporting the cutter 3 is fixed to the frame 24 at a front end portion 24a thereof. Further, the middle roller 26 is connected with a motor 27 constituting a driving portion.

That is, as shown by FIG. 1, the endless belt 23 of the carrying means 20 is endlessly made to travel to be substantially in parallel with feed direction X of the feed mechanism 6 in a plane view thereof by being driven by the motor 27. Further in details, as shown by FIG. 2, the endless belt 23 is made to travel from the rear roller 22 rearward from the cutter 3 to the cutter 3, inserted to between the direction switching roller 21 and the holder 8 by way of the middle roller 25, and guided to a position of being proximate to the cut blade 3b of the cutter 3. Further, the endless belt 23 is folded back upward by the direction switching roller 21, and is reeled back to a rear side of the cutter 3 by the rear roller 22 by way of the middle roller 26. Further, a rotational number of the motor 27 is set such that a traveling speed of the endless belt 23 becomes substantially equal to a speed of moving the feed mechanism 6 in feed direction X.

Figure 3:
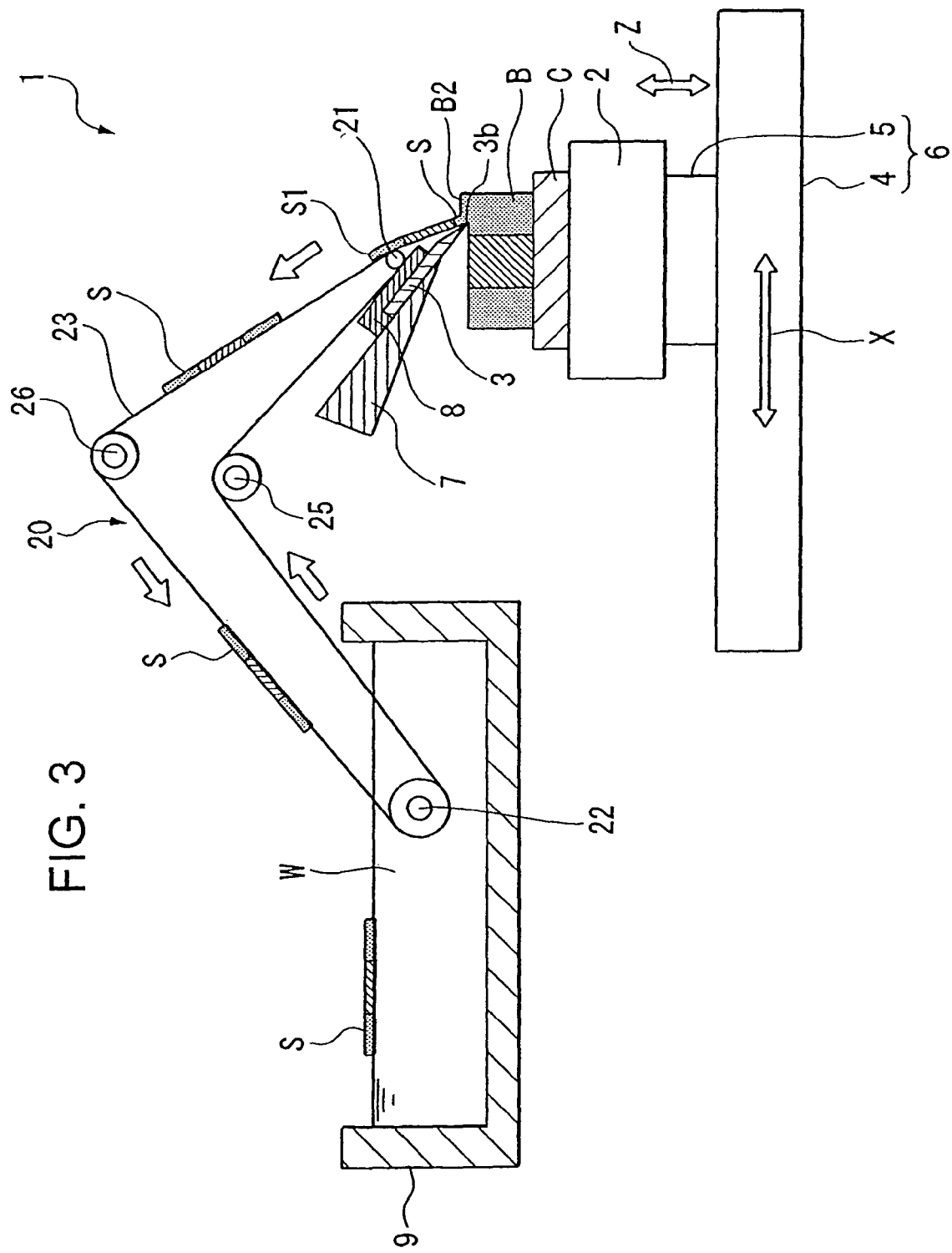
FIG. 3 is a sectional view of the sectioning instrument according to the first embodiment of the invention.

Next, operation of the sectioning instrument 1 according to the embodiment will be explained. As shown by FIG. 2, a position of the embedded block B in height direction Z is adjusted by the Z stage 5 of the feed mechanism 6, and positions of the cutter 3 and the embedded block B relative to each other are determined to be able to slice the embedded block B by a predetermined thickness (about 3 through 5 μm) by the cutter 3. Further, the embedded block B fixed to the sample base 2 is moved in feed direction X by a predetermined moving speed by driving the X stage 4 of the feed mechanism 6, and the endless belt 23 is made to travel by driving the motor 27. Since the cutter 3 is fixed to the frame 24 of the carrying means 20 by the fixed base 7, the embedded block B is moved relative to the cutter 3 and the carrying means 20. Further, as shown by FIG. 3, the section S is fabricated by sectioning the embedded block B by the cutter 3. At this occasion, a surface B2 of the embedded block B is not pressed and therefore, there is not a concern of deforming the surface 2 of the embedded block B, further, the surface B2 can be sliced while observing the surface B2. Therefore, the embedded block B is sliced by an accurate and uniform thickness. Further, the section S which is being fabricated is curled up upward by the cutter 3 and is moved to a rear side of the cutter 3.

Next, since the direction switching roller 21 is provided to be proximate to the cut blade 3b on an upper side of the cutter 3 and therefore, a front end S1 of the section S is folded back by the direction switching roller 21 in accordance with movement of the section S to the rear side of the cutter 3 and is brought into contact with the endless belt 23 reeled back in feed direction X. Further, by fabricating the section S by the cutter 3, the fabricated section S is brought into a state of being mounted on the endless belt 23 traveling to the rear side of the cutter 3. Further, by completely sectioning the embedded block B by the cutter 3, the section S is cut to be separated from the block B and is carried to the rear side of the cutter 3 along with the endless belt 23. Further, a speed of traveling of the endless belt 23 is a speed substantially equal to a moving speed by the feed mechanism 6, that is, a speed of fabricating the section S fabricated by the cutter 3. Therefore, the fabricated section S is not cut by being pulled by the endless belt 23 because the speed of traveling of the endless belt 23 is faster. Or, the section S is not wrinkled between the endless belt 23 and the cut blade 3b and the cutter 3 because the speed of traveling of the endless belt 23 is slower.

Further, the section S mounted on the endless belt 23 is carried to water W of the liquid tank 9 along with the endless belt 23 by being carried to a location at which the rear roller 22 is disposed, detached from the endless belt 23 and floated in water W and is delivered to a next step. Further, the section S is operated with a surface tension of water by being floated on water W in the liquid tank 9 and therefore, deformation of wrinkle, warp, strain produced in being sliced can be corrected. Further, since the carrying means 20 is constituted to travel endlessly by the endless belt 23, after detaching the carried section S in water W of the liquid tank 9, the endless belt 23 can travel again to the cutter 3 and continuously carry the fabricated section S. Further, by dipping the endless belt 23 in water W of the liquid tank 9, the endless belt 23 always maintains a wet state. Therefore, since the surface tension is operated between the section S and the endless belt 23, the section S can further firmly be carried by the endless belt 23.

As described above, according to the sectioning instrument 1, as the carrying means 20, the direction switching roller 21 and the rear roller 22 are provided, and by folding back the endless belt 23 to the upper side of the cutter 3 and reeling back the endless belt 23 to the rear side of the cutter 3, the section S can be fabricated by the cutter 3 and carried while observing the surface B2 of the embedded block B. Further, in sectioning the embedded block B by the cutter 3, the surface B2 of the embedded block B is not pressed at all. Therefore, the section S can automatically be fabricated by the accurate and uniform thickness and can be carried to the next step.

Second Embodiment

Figure 4:
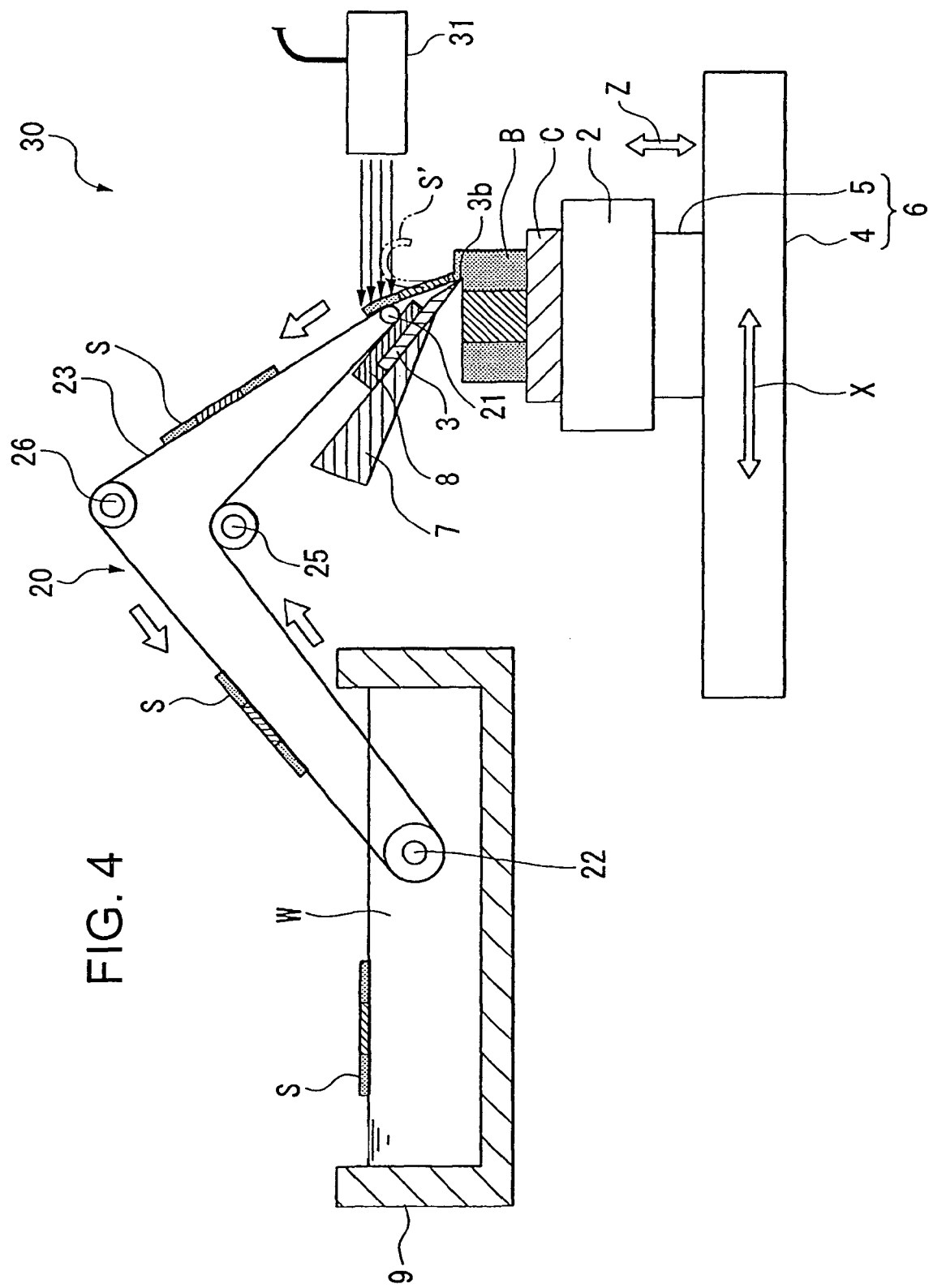
FIG. 4 is a sectional view of a sectioning instrument according to a second embodiment of the invention.

FIG. 4 shows a second embodiment according to the invention. In the embodiment, members common to members used in the above-described embodiment are attached with the same notations and an explanation thereof will be omitted.

As shown by FIG. 4, according to a sectioning instrument 30 of the embodiment, a blower 31 constituting blowing means is provided at a position of being opposed to the direction switching roller 21 frontward from the cutter 3. Further, the blower 31 can press the endless belt 23 folded back by the direction switching roller 21 to the section S by blowing wind to the section S sliced by the cutter 3. Therefore, the fabricated section S is mounted on the endless belt 23 further firmly and is carried to the rear side of the cutter 3 by the endless belt 23. Particularly, although there is a case in which in sectioning by the cutter 3, the section is curled to a front side of the cutter 3 as in a section S', the section can be prevented from being curled by blowing wind thereto by the blower 31.

Third Embodiment

Figure 5:
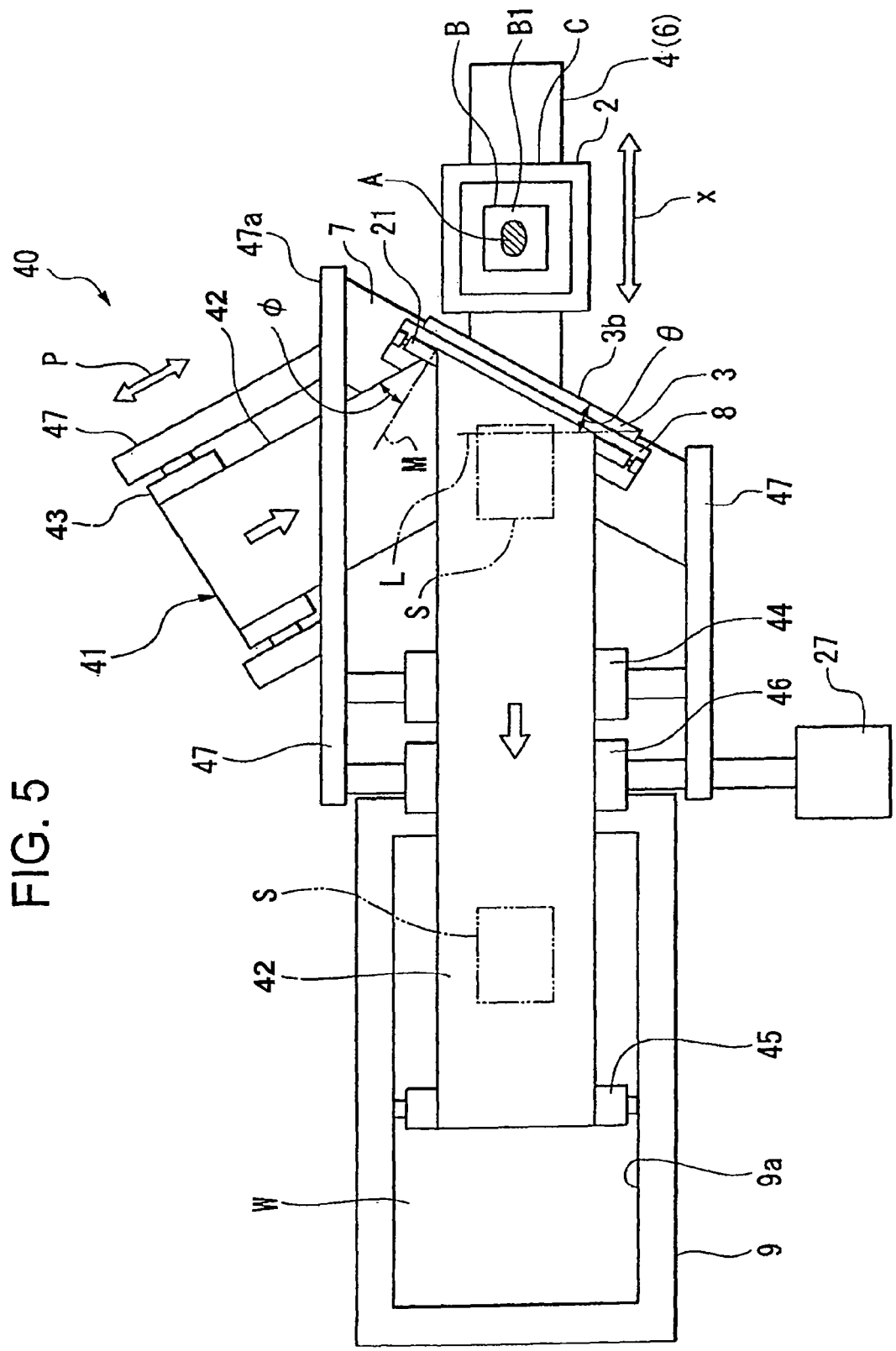
FIG. 5 is a plane view of a sectioning instrument according to a third embodiment of the invention.
Figure 6:
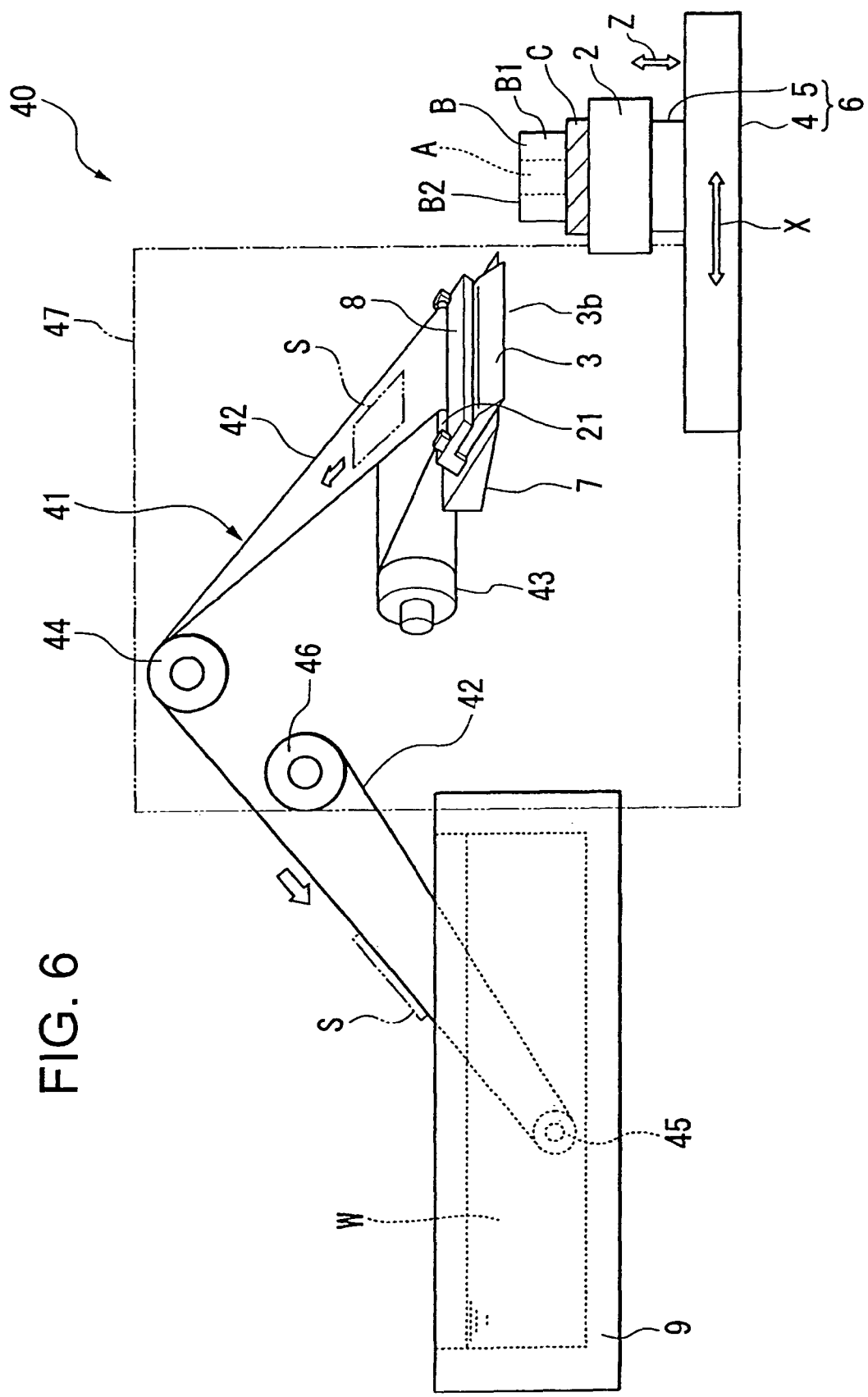
FIG. 6 is a side view of the sectioning instrument according to the third embodiment of the invention.

FIG. 5 and FIG. 6 show a third embodiment according to the invention. According to the embodiment, members common to members used in the above-described embodiments are attached with the same notations and an explanation thereof will be omitted.

As shown by FIG. 5, according to a sectioning instrument 40 of the embodiment, the direction of the cut blade 3b of the cutter 3 is provided by including a draw angle θ relative to an axis line L orthogonal to feed direction X of the feed mechanism 6 on a cut face formed by the cutter 3. Further, as shown by FIG. 5 and FIG. 6, carrying means 41 includes a belt 42, a supply roller 43 wound with the belt 42 for supplying the belt 42, middle rollers 44, 45 provided on the rear side of the cutter 3, and a rear roller 46 for winding the belt 42. Further, the supply roller 43 is axially attached rotatably to a frame 47, and a supply direction P for supplying the belt 42 from the supply roller 43 to the direction switching roller 21 is arranged to be inclined to an axis line M orthogonal to the direction of the cut blade 3b of the cutter 3 by an angle φ substantially equal to the draw angle θ. The middle roller 45 is axially attached rotatably to the inner wall 9a of the liquid tank 9 and is dipped in water W of the liquid tank 9. Further, the middle roller 44 is axially attached rotatably to the frame 47 and is arranged to be disposed upward from the direction switching roller 21 and the middle roller 45 between the direction switching roller 21 and the middle roller 45. Further, the rear roller 46 is axially attached rotatably to the frame 47, connected to the motor 27 and is arranged to be disposed to a lower side of the middle roller 44. Further, the middle rollers 44, 45 and the rear roller 46 are arranged to be able to make the belt 42 folded back by the direction switching roller 21 travel substantially in parallel with feed direction X in a plane view thereof. Further, also the fixed base 7 for supporting the cutter 3 is fixed to a front end portion 47a of the frame 47.

That is, the belt 42 of the carrying means 41 is supplied to travel in the supply direction P inclined to the axis line M by the angle φ from the supply roller 43 by rotating the rear roller 46 by driving the motor 27. Further, the belt 42 is folded back upward by the direction switching roller 21 to travel to the rear side of the cutter 3 in the direction substantially in parallel with the feed direction X. Further, the belt 42 is dipped in water W at the middle roller 45 by way of the middle roller 44, folded back again and is wound by the rear roller 46.

According to the sectioning instrument 40, since the cutter 3 is provided to include the draw angle θ, a resistance in sectioning the embedded block B is restrained and the embedded block B can be sliced by a further accurate and uniform thickness and by an excellent cut face. At this occasion, the direction switching roller 21 is substantially in parallel with a direction of the cut blade 3b of the cutter 3, further, the belt 42 is reeled back by the rear roller 46 substantially in parallel with a direction of fabricating the section S, that is, feed direction X of the feed mechanism 6. Therefore, the section S fabricated by the cutter 3 can firmly be mounted on the belt 42 and can smoothly be carried without being cut by operating twist or the like by traveling of the belt 42. On the other hand, the belt 42 is not twisted even when the direction switching roller 21 is provided to include the draw angle θ along with the cut blade 3b by inclining the supply direction P of making the belt 42 travel from the supply roller 43 to the direction switching roller 21 by the angle φ substantially equal to the draw angle θ relative to the axis line M orthogonal to the direction of the cut blade 3b. Therefore, the belt 42 can be made to travel smoothly from the supply roller 43 to the direction switching roller 21, further, from the direction switching roller 21 to the rear roller 46 by way of the middle rollers 44, 45.

Fourth Embodiment

Figure 7:
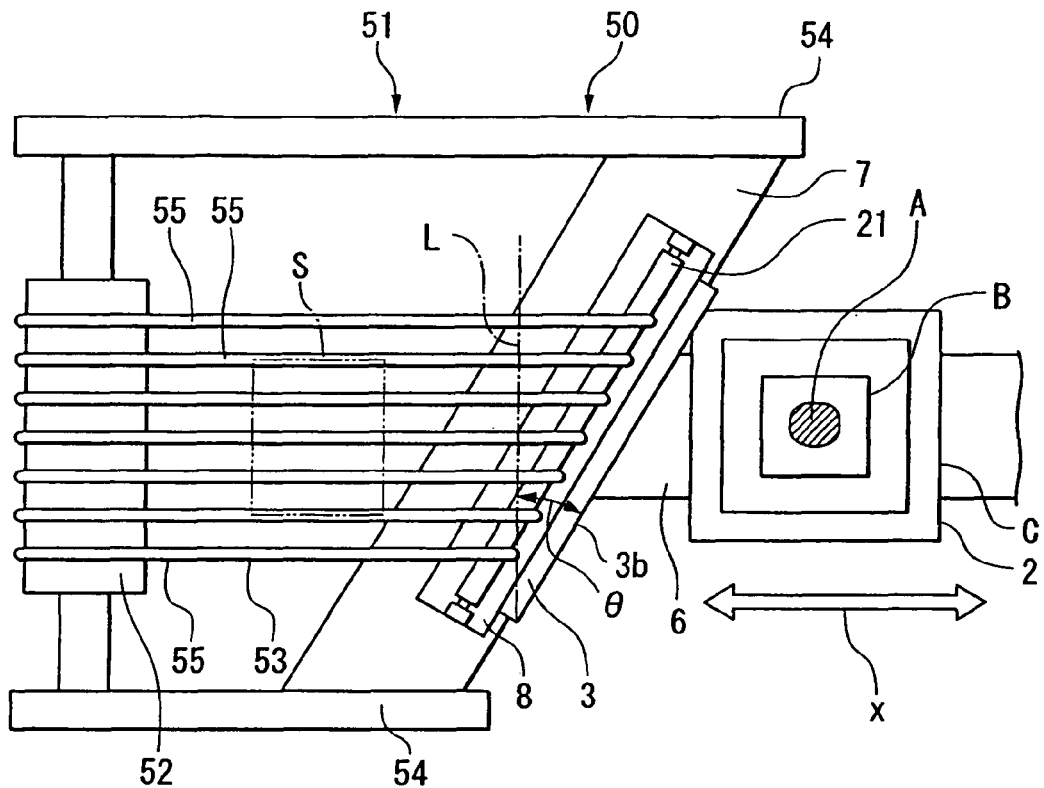
FIG. 7 is a plane view of a sectioning instrument according to a fourth embodiment of the invention.

FIG. 7 shows a fourth embodiment according to the invention. According to the embodiment, members common to members used in the above-described embodiments are attached with the same notations and an explanation thereof will be omitted.

As shown by FIG. 7, according to a sectioning instrument 50 of the embodiment, the cutter 3 is provided to include the draw angle θ relative to the axis line L, and carrying means 51 includes the direction switching roller 21, a rear roller 52, and an endless belt 53 wound between the direction switching roller 21 and the rear roller 52. The fixed base 7 for supporting the cutter 3 is fixed to a frame 54. Further, the rear roller 52 is axially attached rotatably to the frame 54 and is arranged to be able to make the endless belt 53 travel in feed direction X. Further, the endless belt 53 is formed by a plurality of ring-like members 55 substantially in a string-like shape arranged by providing predetermined intervals thereamong. Respective of the ring-like members 55 include different peripheral lengths in correspondence with a distance between the rear roller 52 and the direction switching roller 21. Therefore, the endless belt 53 can travel endlessly between the rear roller 52 and the direction switching roller 21 smoothly. That is, according to the sectioning instrument 50, since the cutter 3 includes the draw angle θ, the resistance in sectioning can be restrained, and the fabricated section can continuously be carried by constituting the endless belt 53 formed by the ring-like members 55.

Fifth Embodiment

Figure 8:
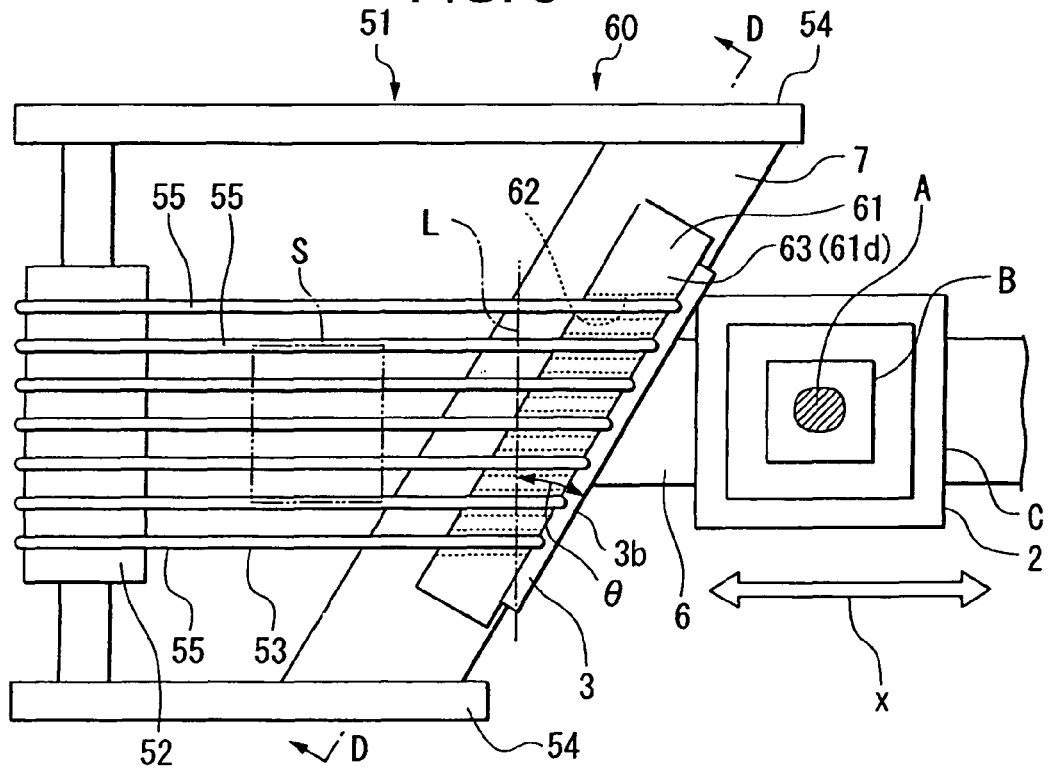
FIG. 8 is a plane view of a sectioning instrument according to a fifth embodiment of the invention.
Figure 9:
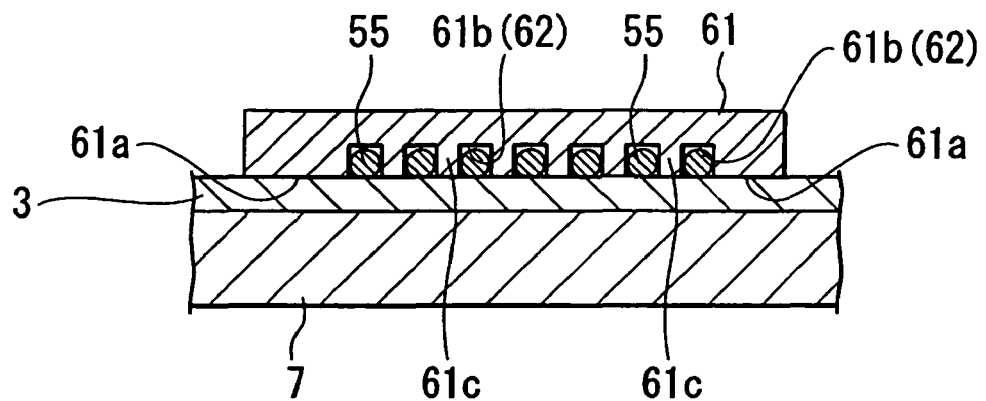
FIG. 9 is a partial sectional view viewing the sectioning instrument according to the fifth embodiment of the invention from a front side.
Figure 10:
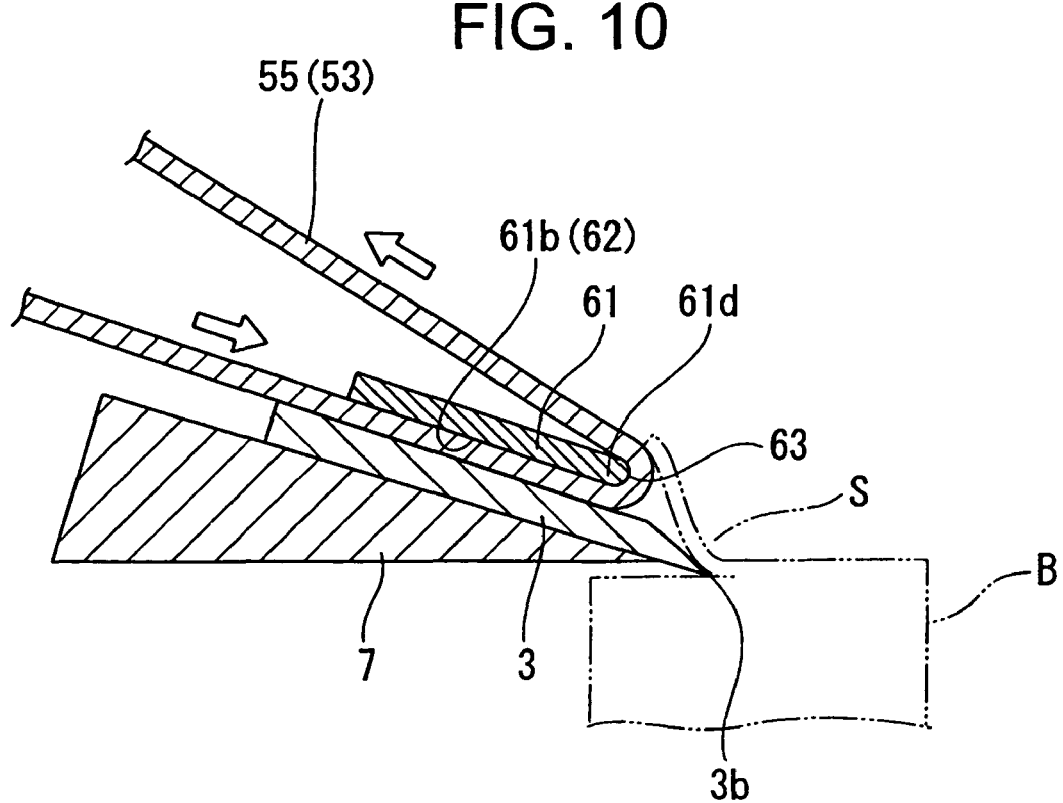
FIG. 10 is a partial sectional view viewing the sectioning instrument according to the fifth embodiment of the invention from a side direction.

FIG. 8 through FIG. 10 show a fifth embodiment according to the invention. According to the embodiment, members common to members used in the above-described embodiments are attached with the same notations and an explanation thereof will be omitted.

As shown by FIG. 8 and FIG. 9, according to a sectioning instrument 60 of the embodiment, in a sectional shape viewing a holder 61 for fixing the cutter 3 to the fixed base 7 from a front side (D-D section shown in FIG. 8), both end portions 61a are projected downward, a recess portion 61b is formed at a center, and a plurality of projected portions 61c are formed at the recess portion 61b at predetermined intervals. Further, the cutter 3 is fixed to the fixed base 7 by bringing the both end portions 61a and the projected portion 61c into contact with the upper face 3a of the cutter 3 and squeezing the cutter 3 between the holder 61 and the fixed base 7, and a plurality of through holes 62 penetrated from a front side to a rear side of the cutter 3 are formed by the recess portions 61b and the projected portions 61c of the holder 61. Further, as shown by FIG. 10, a front end portion 61d of the holder 61 is provided with a direction switching portion 63 a section of which is formed in a circular shape. Further, respective of the ring-like members 55 forming the endless belt 53 are inserted to the respective of the through holes 62 from the rear side of the cutter 3 and folded back by the direction switching portion 63.

According to the sectioning instrument 60, respective of the ring-like members 55 of the endless belt 53 are made to pass through the through holes 62 formed between the holder 61 and the cutter 3 from the rear side of the cutter 3 and folded back by the direction switching portion 63 formed at a front end of the holder 61. Therefore, the endless belt 53 and the cutter 3 can further proximately be arranged at a vicinity of the cut blade 3b of the cutter 3 and therefore, the section S fabricated by the cutter 3 and moved to a rear side can further firmly be mounted on the endless belt 53. Further, although according to the embodiment, respective of the plurality of ring-like members 55 forming the endless belt 53 are inserted through respective of the plurality of through holes 62, a similar effect can be expected by constructing a constitution in which the holder 61 is not provided with the projected portion 61c by constituting the endless belt 53 by a strip-like belt.

Although the embodiments of the invention are described in details in reference to the drawings as mentioned above, the specific constitution is not limited to the embodiment but includes a change in design or the like within the range not deviated from the gist of the invention.

Further, although the feed mechanism 6 is made to be able to move the sample base 2 in feed direction X and height direction Z, the feed mechanism 6 is not limited thereto but may be constructed by a constitution of fixing the sample base 2 and simultaneously moving the cutter 3 and the carrying means 20. At least, the sample base 2 fixed with the embedded block B may be made to be able to move relative to the cutter 3 and the carrying means 20. Further, although the moving speed by the feed mechanism 6 and the traveling speed of the belt are set substantially equal to each other, the speeds are adjusted relative to each other within a range of mounting to carry the fabricated section S on the belt without damaging the section S. Further, although the liquid tank 9 is provided on the rear side of the cutter 3, since the section S is brought into a state of being only mounted on the belt, the invention is not limited thereto but the section S can easily be taken out to deliver to the next step also by other constitution. Further, although the liquid tank 9 is filled with water W, a liquid mainly constituted by water will do, further, the liquid can variously be selected so far as the liquid is a liquid having a property of not dissolving the embedding medium B1 of the section S.

What is claimed is:

1. A sectioning instrument comprising a sample base for fixing an embedded block embedded with a living body sample, a cutter for fabricating a section by sectioning the embedded block fixed to the sample base, carrying means for carrying the section fabricated by the cutter to a rear side of the cutter to deliver to a next step, and a feed mechanism for moving the embedded block to the cutter, at a cutting speed, the sample base in a predetermined feed direction and sectioning the embedded block by the cutter;
wherein the carrying means comprises:
a belt for carrying the section;
a direction switching portion provided on an upper side of the cutter substantially in parallel with a direction of a cut blade of the cutter, proximate to the cut blade and having a gap capable of inserting the belt between the cutter and the direction switching portion; and
a rear roller provided in the rear side of the cutter;
wherein the belt is made to travel, at a carrying speed that is substantially equal to the cutting speed during fabrication of the section, from the rear side of the cutter to the cutter, inserted between the cutter and the direction switching portion, folded back to an upper side by the direction switching portion, and reeled back to the rear side of the cutter by the rear roller, wherein the belt is further made to travel continuously after fabrication of the section at least until the fabricated section is carried to the rear side of the cutter to deliver to the next step; and
wherein the belt is wet at a portion on the belt at which the section comes into contact with the belt.

2. The sectioning instrument according to claim 1, wherein a position on a front side of the cutter opposed to the direction switching portion is provided with blowing means for blowing wind to the section sliced by the cutter to press the section to the belt folded back by the direction switching portion of the carrying means.

3. The sectioning instrument according to claim 1, further comprising:
a fixed base for supporting the cutter; and
a holder a section of which is substantially in a channel-like shape projecting both end portions to a lower side and formed with a recess portion at a center thereof, in which the both end portions are brought into contact with an upper face of the cutter, the cutter is squeezed between the holder and the fixed base, and which is formed with a through hole penetrated from a rear side to a front side of the cutter between the holder and the cutter by the recess portion; and
wherein a front end of the holder is formed with the direction switching portion, the belt is inserted through the through hole from the rear side of the cutter and is folded back by the direction switching portion.

4. The sectioning instrument according to claim 1, wherein the carrying means comprises a supply roller wound with the belt for supplying the belt; and
wherein the belt is made to travel from the supply roller to the direction switching portion, folded back by the direction switching portion and is wound by the rear roller.

5. The sectioning instrument according to claim 4, wherein a direction of the cut blade of the cutter is provided to include a predetermined draw angle relative to an axis line orthogonal to the feed direction of the feed mechanism on a cut face formed by the cutter;
wherein a direction of supplying the belt traveling from the supply roller to the direction switching portion is set to be inclined to an axis line orthogonal to the direction of the cut blade by an angle substantially equal to the draw angle; and
wherein the belt folded back by the direction switching portion is reeled back in parallel with the feed direction of the feed mechanism by the rear roller in a plane view thereof.

6. The sectioning instrument according to claim 1, wherein the belt of the carrying means is an endless belt wound between the rear roller and the direction switching portion.

7. The sectioning instrument according to claim 6, wherein a direction of the cut blade of the cutter is provided to include a predetermined draw angle relative to an axis line orthogonal to the feed direction of the feed mechanism on a cut face formed by the cutter; and
wherein the belt of the carrying means is formed by a plurality of ring-like members substantially in a string-like shape arranged at predetermined intervals thereamong, respective of the ring-like members are provided with different peripheral lengths in correspondence with a distance between the rear roller and the direction switching portion, and reeled back substantially in parallel with the feed direction of the feed mechanism by the rear roller in a plane view thereof.

8. The sectioning instrument of claim 1, wherein during carrying of the section by the belt:
a front portion of the section is brought into contact with the belt of the carrying means during sectioning of the embedded block by the cutter;
a middle portion of the section is subsequently brought into contact with the belt traveling to the rear side of the cutter; and
after sectioning, the whole section is carried to the rear side of the cutter by the belt.

9. A sectioning instrument comprising:
a sample base configured to fix an embedded block embedded with a living body sample;
a cutter configured to fabricate a section by sectioning the embedded block fixed to the sample base;
a carrying means for carrying the section fabricated by the cutter to a rear side of the cutter to deliver to a next step, wherein the carrying means comprises:
a belt for carrying the section;
a direction switching portion provided on an upper side of the cutter substantially in parallel with a direction of a cut blade of the cutter, proximate to the cut blade and having a gap capable of inserting the belt between the cutter and the direction switching portion; and
a rear roller provided in the rear side of the cutter;
wherein the belt is made to travel, at a carrying speed during fabrication of the section, and is made to travel continuously after fabrication of the section at least until the fabricated section is carried to the rear side of the cutter to deliver to the next step, and
wherein the carrying means is configured to make wet a portion of the belt at which the section comes into contact with the belt; and
a feed mechanism for moving the embedded block to the cutter, at a cutting speed that is substantially equal to the carrying speed, the sample base in a predetermined feed direction and sectioning the embedded block by the cutter.

10. The sectioning instrument of claim 9, wherein during carrying of the section by the belt:

a front portion of the section is brought into contact with the belt of the carrying means during sectioning of the embedded block by the cutter;

a middle portion of the section is subsequently brought into contact with the belt traveling to the rear side of the cutter; and after sectioning, the whole section is carried to the rear side of the cutter by the belt.

11. The sectioning instrument of claim 9, wherein the feed mechanism is configured to move the embedded block in a direction substantially perpendicular to the predetermined feed direction.

12. The sectioning instrument of claim 11, wherein the feed mechanism is configured to move the embedded block such that a thickness of the section fabricated by the cutter is between approximately 3 μm and approximately 5 μm.

* * * * *